United States Patent [19]
Buchanan et al.

[11] Patent Number: 5,841,661
[45] Date of Patent: Nov. 24, 1998

[54] WAFER IMAGE (ADS) VISION SYSTEM TO AUTOMATED DIMENSIONING EQUIPMENT (ADE) COMMUNICATION INTERFACE SYSTEM

[75] Inventors: Curtis Paul Buchanan, Camas; Thomas Read Paine, Vancouver; Scott Alan Cann, Washougal, all of Wash.

[73] Assignee: Seh America, Inc., Vancouver, Wash.

[21] Appl. No.: 703,028

[22] Filed: Aug. 26, 1996

[51] Int. Cl.$^6$ .......................... G06F 19/00; G06G 7/64; G06G 7/66

[52] U.S. Cl. .................. 364/468.28; 364/468.02; 364/468.04; 364/468.26

[58] Field of Search .................. 364/522, 488, 364/489, 490, 491, 468.28, 468.02, 468.26, 468.04; 382/156, 148, 358, 142

[56] References Cited

U.S. PATENT DOCUMENTS

| | | | |
|---|---|---|---|
| 4,571,685 | 2/1986 | Kamoshida | 364/468 |
| 4,618,938 | 10/1986 | Sandland et al. | 364/552 |
| 4,659,220 | 4/1987 | Bronte et al. | 356/237 |
| 4,878,736 | 11/1989 | Hekker et al. | 350/162.13 |
| 4,901,242 | 2/1990 | Kotan | 364/468 |
| 4,916,640 | 4/1990 | Gasperi et al. | 364/521 |
| 5,062,052 | 10/1991 | Sparer et al. | 364/473 |
| 5,095,204 | 3/1992 | Novani | 250/223 |
| 5,097,421 | 3/1992 | Maney et al. | 364/478 |
| 5,105,362 | 4/1992 | Kotani | 364/468 |
| 5,219,765 | 6/1993 | Yoshida et al. | 437/8 |
| 5,372,471 | 12/1994 | Wu | 414/786 |
| 5,386,360 | 1/1995 | Wilson et al. | 364/146 |
| 5,443,346 | 8/1995 | Murata et al. | 414/222 |
| 5,474,647 | 12/1995 | Poultney et al. | 156/626.1 |

*Primary Examiner*—Reba I. Elmore
*Assistant Examiner*—Ramesh Patel
*Attorney, Agent, or Firm*—Bell Seltzer Intellectual Property Group of Alston & Bird, LLP

[57] ABSTRACT

In a semiconductor manufacturing process in which wafers are analyzed using a wafer image (ADS) vision system and automated dimensioning equipment (ADE), an automated communication interface system is provided. The interface system uses a programmable logic controller in combination with relays to communicate signals between the ADS vision system and the automated dimensioning equipment in response to signal indications in both. The programmable logic controller includes a plurality of timers for generating signals of selected duration as well as time delays of selected duration. The relays permit signals to be communicated in the face of signal system incompatibility between components. When a wafer in the automated dimensioning equipment is ready for optical analysis, the interface system responds by sending a start signal to the ADS vision system, which responds by analyzing the wafer and providing accept or reject indications. Signals representing the accept or reject indications are communicated to the automated dimensioning equipment, followed by an enter signal which is required by such equipment. The interface keeps track of the number of times the ADS vision system takes longer than a first predetermined time interval to provide an accept or reject indication, and sets off an alarm when the accept or reject indication does not occur until after a second time delay.

16 Claims, 4 Drawing Sheets

WAFER IMAGE (ADS) VISION SYSTEM TO AUTOMATED DIMENSIONING EQUIPMENT (ADE) COMMUNICATION INTERFACE SYSTEM

BACKGROUND OF THE INVENTION

1. Field of the Invention

The present invention relates to interface systems for analyzing equipment in a semiconductor manufacturing process, and more particularly to an automated interface for use between a wafer image (ADS) vision system and automated dimensioning equipment (ADE) for analyzing semiconductor wafers.

2. History of the Prior Art

It is known to use automated dimensioning equipment (ADE) in combination with a wafer image (ADS) vision system in analyzing wafers in a semiconductor manufacturing process. The ADE comprises a wafer track system in which wafers are unloaded from send cassettes onto a belt which is movable through various inspection stations, one of which includes the ADS vision system. After each wafer is examined for proper alignment, it is advanced to the ADS vision system, where the wafer surface undergoes an optical analysis for defects such as mounds, lines and dimples. Following optical analysis by the ADS vision system, the ADE subjects the wafer to further testing for such characteristics as thickness, resistivity and wafer conductivity type, before loading the wafer into an appropriate receive cassette for removal by an operator.

In the ADS vision system, a source of high brightness collimated light is directed onto the highly reflective surface of the wafer (which is typically a polished or epitaxial single crystal semiconductor wafer), and the reflected image of the wafer surface is projected onto a projector screen or optical apparatus. In this manner, the image is made visible or is stored electronically using a change coupled device (CCD) receiver. Surface irregularities which exceed detection limits show up in the form of an optical image representing the individual defects.

In an earlier example of wafer optical analysis equipment, the wafer was held on a rotatable chuck by a vacuum. As the chuck rotated, collimated light was directed onto the wafer surface, and the surface reflection was projected onto a screen mounted above the wafer track system. An operator then determined whether the wafer was acceptable or had to be rejected, under criteria established by limit samples. Limit samples are controlled generated specimens used to train the operator to optically evaluate borderline levels of accept/reject criteria for predetermined defects on the semiconductor wafers.

Such earlier techniques eventually gave way to more modern techniques such as that employed by the ADS vision system manufactured by ADS Company, Ltd. of Japan. As used herein, the terms "wafer image vision system" and "ADS vision system" refer to this type of vision system. In the ADS vision system, a camera is used to electronically convert the surface image into a bit map. The bit map is electronically compared to the stored image of a limit sample. The equipment which includes a PIP 9000 Flexible Image Processor made by ADS Company, indicates, via an output device, whether the inspected wafer is acceptable or has to be rejected. The operator then manually logs each wafer into the ADE via keyboard entry under the pass/fail category. The ADE can directly communicate with an electronic business system in order to collect data. Typically, the ADE measures wafer characteristics such as flatness, resistivity and conductivity type, using contactless probes. The data collected by the ADE is fed to the electronic business system for analysis and to generate certificates of analysis which accompany the products to the customers.

In wafer analysis arrangements of the type described, a human operator is required to interface the ADS vision system with the ADE. When each wafer reaches a station in the ADE where the ADS vision system is located, the operator scans a display to determine that the wafer is ready for inspection and pushes a start button on a test box coupled to the ADS vision system. The ADS vision system optically analyzes the wafer surface and provides an indication on the box that the wafer is acceptable or is rejected. Using a keyboard, the operator keys in an accept or reject indication, followed by an enter command. The ADE collects this information, and together with other information on characteristics such as thickness, resistivity and conductivity type, determines which of various receive cassettes the wafer should be loaded into at the output end of the ADE.

The need for an operator to provide human intervention between the ADS vision system and the ADE adds to the cost of the semiconductor manufacturing process. Moreover, the human interaction is subject to errors, inasmuch as the operator may occasionally misread information or key in incorrect information to the ADE. Also, the need for an operator places limits on the amount of information which can be communicated between the ADS vision system and the ADE. As wafer analysis systems become more sophisticated and require communication of additional information between systems, the limits of a human operator are quickly exceeded. Thus, ADS vision systems may soon be capable of providing more than just accept or reject indications. The possibility of providing such further data which would categorize the wafers in greater detail, beyond a simple accept or reject categorization, would require replacement of the human operator by a much more sophisticated and automated interfacing arrangement.

It is known in the art to use automated interfaces between wafer processing equipments. For example, U.S. Pat. No. 4,571,685 of Kamoshida employs inspection apparatus for automatically conveying the results of a first step for processing material to a second material processing step, in the manufacture of semiconductor wafers. Still other examples are provided by U.S. Pat. No. 4,901,242 of Kotan, U.S. Pat. No. 5,097,421 of Maney et al., U.S. Pat. No. 5,105,362 of Kotani, U.S. Pat. No. 5,219,765 of Yoshida, and U.S. Pat. No. 5,474,647 of Poultney et al. However, while the arrangements shown in these patents do much to minimize or eliminate the need for operator intervention, they fail to address the particular problems of wafer analyzing systems, such as between an ADS vision system and an ADE, in the fully automated fashion which is desired.

Accordingly, it is an object of the invention to provide an improved communication interface system between analyzing equipments in a semiconductor manufacturing, process. More specifically, it is an object of the invention to provide an automated interface, which eliminates the need for a human operator, and which effectively interfaces between analysis equipment such as an ADS vision system and automated dimensioning equipment (ADE).

BRIEF DESCRIPTION OF THE INVENTION

The present invention provides a communication interface system for interfacing analysis equipments such as in a semiconductor manufacturing process. The interface system is completely automated so that the need for a human operator is eliminated. The interface uses program control to generate and communicate signals of selected duration in conjunction with the generation of time delay intervals for determining the timeliness or untimeliness of the various signals communicated. The incompatibility posed by the different electrical signaling systems of the different components is compensated for through use of components such as relays which enable signals to be communicated between the components without direct electrical connection of the components. The independent generation of signals within the interface in response to signal indications within the components acts as a signal conditioning process by generating and communicating signals of desired configuration which are free of noise.

In a preferred arrangement of a communication interface system according to the invention, an ADS vision system is interfaced with automated dimensional equipment (ADE) by an interface comprised of a programmable logic controller having an operating program stored therein or in association therewith. The interface also includes a plurality of solid state relays coupling the controller to the ADS vision system and to the ADE, as well as a plurality of lamps used to provide visual indications of various conditions. Each relay has the coil thereof coupled to the ADS vision system or the ADE, and the electronic switch contacts thereof coupled to the interface, so that signal indications within the ADS vision system and the ADE are communicated through the interface without the need for direct electrical interconnection of the interface with the ADS vision system and the ADE. The controller is programmed to perform a plurality of different timed counts, which are used to generate signals of selected duration as well as time delay intervals of selected duration. In this fashion, the interface provides compatible, basically noise-free signals of desired configuration to the ADS vision system and to the ADE. The time delay intervals are used to determine the timeliness of the optical analysis performed by the ADS vision system.

In accordance with the further details of an interface for use with an ADS vision system and an ADE, the interface is comprised of a programmable logic controller and various relays, in the manner described. The interface responds to a signal indication from the ADE that a wafer is ready for optical analysis by the ADS vision system, by providing a start signal to the ADS vision system. At the same time, the interface begins counts defining first and second predetermined time delay intervals. At the end of an imaging time interval the ADS vision system provides a signal indication that the wafer being analyzed is either accepted or rejected, and the interface responds by providing an accept or reject signal to the ADE. After a predetermined delay following the generation of the accept or reject signal, the interface provides an enter signal to the ADE. If generation of the accept or reject signal does not occur until after the lapse of the first predetermined time interval, but before the second predetermined time interval has lapsed, the interface advances a counter so as to keep a record of the number of such delayed responses. If the accept or reject signal does not occur until after the second predetermined time interval has ended, then an alarm is provided. However, the system is not halted, but continues to operate in the manner described.

DETAILED DESCRIPTION

Figure 1:
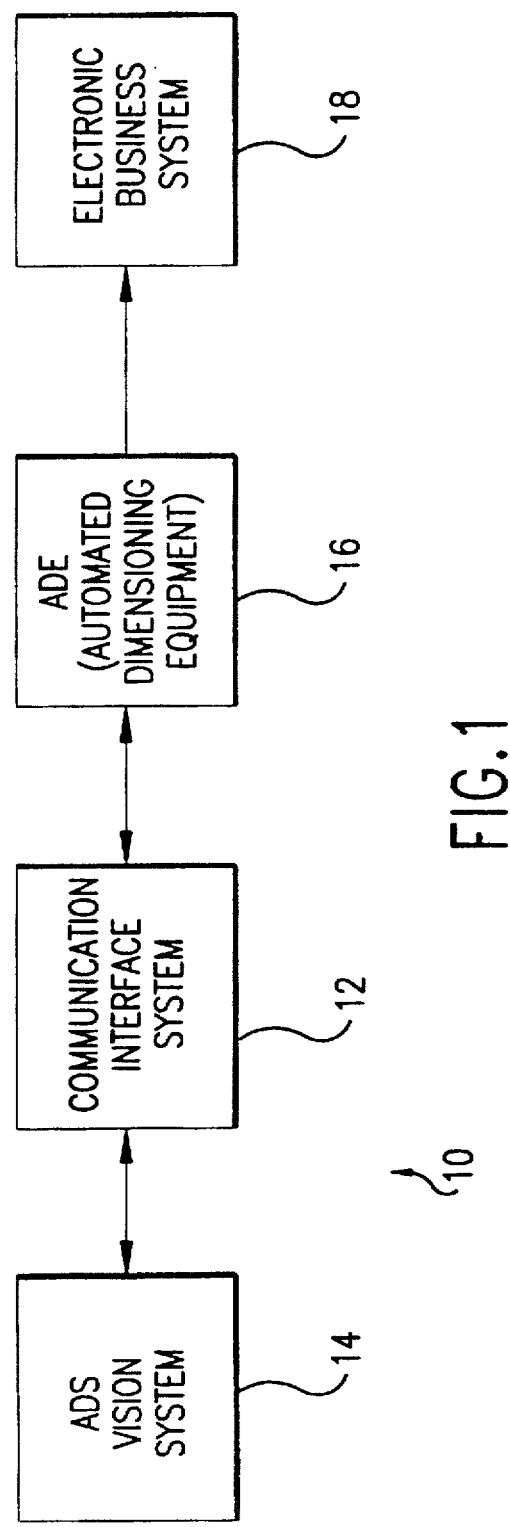
FIG. 1 is a basic block diagram of an arrangement for analyzing semiconductor wafers, which employs a communication interface system according to the invention.

FIG. 1 is a basic block diagram of an arrangement 10 for analyzing semiconductor wafers, which employs a communication interface system 12 according to the invention. The communication interface system 12 provides a completely automated interface between an ADS vision system 14 and an ADE (automated dimensioning equipment) 16, so that the need for a human operator is eliminated. Apart from the presence of a communication interface system 12 according to the invention, the arrangement 10 of FIG. 1 otherwise operates in conventional fashion to analyze the characteristics of semiconductor wafers in a semiconductor manufacturing process.

The ADE 16 is a wafer track system of conventional design in which wafers are removed from send cassettes and placed on a belt which is movable between various inspection stations one of which includes the ADS vision system 14. Typically, a first station within the ADE is used to correctly align each wafer on the movable belt. At a subsequent station, the ADS vision system 14 optically analyzes the surface of each wafer, and provides an accept or reject indication, which the communication interface system 12 communicates to the ADE. At subsequent stations, the ADE analyzes other characteristics of each wafer such as thickness, resistivity and wafer conductivity type. The ADE stores and evaluates the accept or reject signal from the ADS vision system 14, together with information as to the other characteristics determined by the ADE, in determining which of a plurality of receive cassettes each wafer is to be placed in at the output end of the ADE. Such information is then passed to an electronic business system 18. The electronic business system 18 collects data for reporting statistical parameter distributions to customers in connection with shipments of wafers to the customers.

Figure 2:
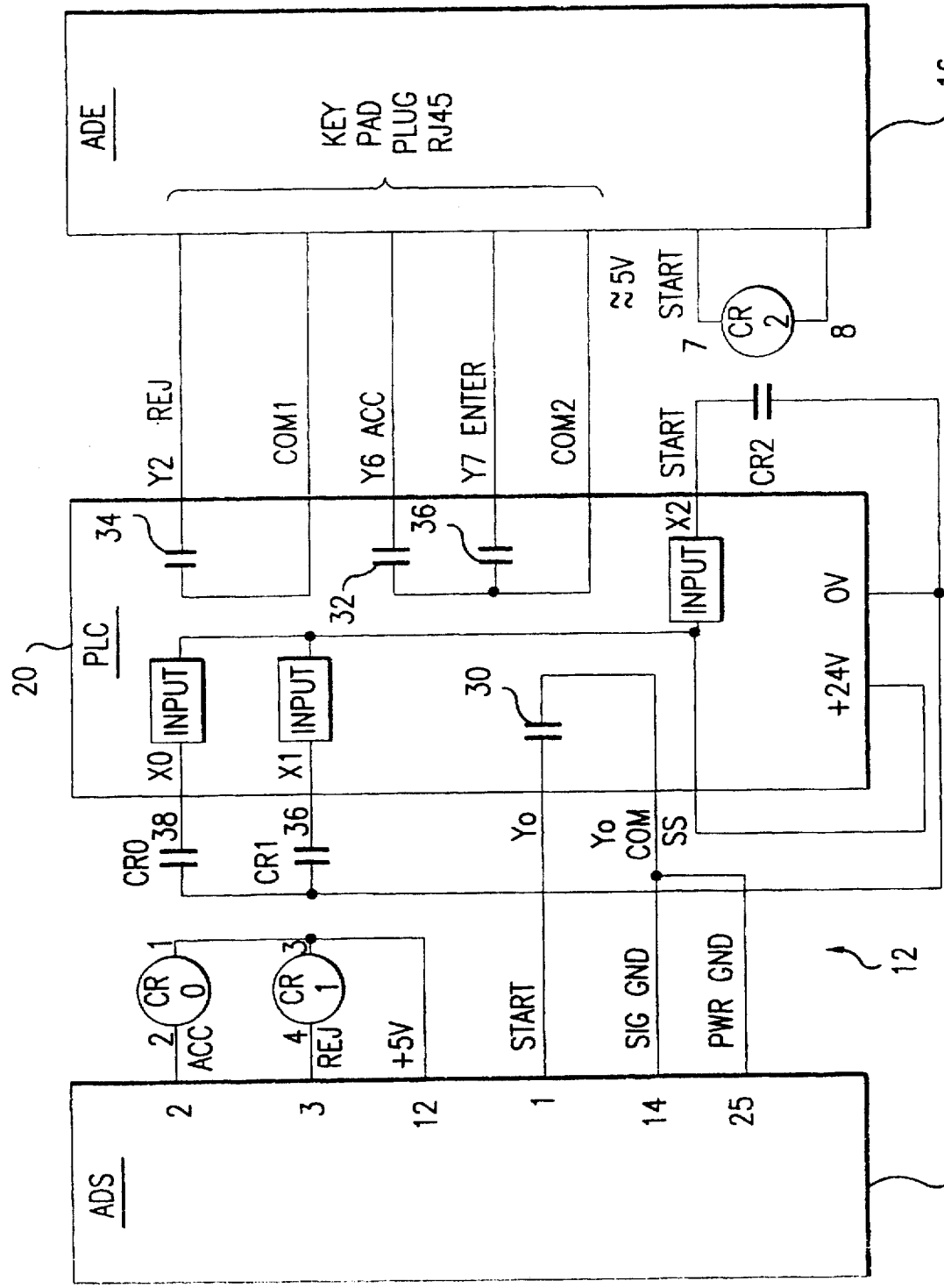
FIG. 2 is a schematic diagram of the interface system of FIG. 1 in conjunction with associated portions of the ADS vision system and the ADE.

FIG. 2 provides a detailed example of the communication interface system 12 in conjunction with the ADS vision system 14 and the ADE 16. In the example of Fig. 2, and as described hereafter in conjunction with FIGS. 3 and 4, the ADS vision system is manufactured by ADS Company, Ltd. of Japan and, as previously noted, the terms "wafer image vision system" and "ADS vision system" refer to that type of vision system. The ADE 16 is a Model 7000 or 7200 manufactured by ADE Corporation of Newton, Mass. and as used herein, the terms "automated dimensioning equipment" and "ADE" refer to this type of equipment.

As shown in FIG. 2, the communication interface system 12 includes a PLC (programmable logic controller) 20 together with various relays. The relays include first and second relays CR0 and CR1 coupled to be actuated by the ADS vision system 14, and a third relay CR2 coupled to be actuated by the ADE 16. In the present example, and as shown in greater detail in FIG. 3, the PLC 20 is a Model FX$_0$-30MR-ES programmable logic controller, manufactured by Mitsubishi Corporation. An operating program for the PLC is stored in an EEPROM memory for the PLC. The solid state relays CR0, CR1 and CR2 are provided by a Model MS-4 relay board manufactured by Crydom Co. It will be appreciated by those skilled in the art, however, that other programmable logic controllers and/or relay boards can be used in communication interface systems according to the invention.

As previously described, the ADE 16 has a belt for moving wafers between various stations, one of which includes the ADS vision system 14. When a wafer is ready for optical analysis by the ADS vision system 14, a signal which starts the motor for rotating the chuck within the ADE provides a START signal indication. This energizes the relay CR2 to close the electronic switch thereof and provide a START signal to the PLC 20. Whereas the coil of the relay CR2 is coupled to the ADE 16, the contacts thereof are coupled to the PLC 20. This enables the START signal to be communicated from the ADE 16 to the PLC 20 without direct electrical coupling therebetween. Consequently, electrical components which may be incompatible due to different signaling systems can communicate with one another.

The PLC 20 responds to the START signal from the relay contacts CR2 by providing a START signal to the ADS vision system 14. The PLC 20 does this by closing a pair of contacts 30 therein to complete a circuit between terminals 1 and 14 of the ADS vision system 14. At the same time, and as described hereafter in connection with FIG. 4, the PLC 20 begins a 6 second count and a 10 second count which are used in evaluating any delay in the response of the ADS vision system 14.

Following receipt of the START signal from the PLC 20, the ADS vision system 14 performs optical analysis of the surface of the wafer, during an imaging time interval which typically lasts 3–4 seconds. Depending upon the surface conditions observed, the ADS vision system 14 provides either an accept (ACC) signal indication at a terminal 2 thereof or a reject (REJ) signal indication at a terminal 3 thereof. The ACC and RFJ signal indications are the same signals used to activate visual indicators on the test box, when an operator is used. An ACC signal indication energizes the coil of the relay CR0, which in turn closes the contacts CR0, coupled to a terminal X0 of the PLC 20. The PLC 20 responds by closing a pair of contacts 32 to provide an accept (ACC) signal at a terminal Y6 thereof. The ACC signal is communicated to the ADE 16. If a reject signal indication is provided at the terminal 3 of the ADS vision system 14 so as to energize the coil of the relay CR1, the relay contacts CR1 are closed so as to communicate a corresponding signal to the PLC 20. The PLC 20 responds by closing a pair of contacts 34 to provide a reject signal (REJ) at a terminal Y2 thereof, which signal is communicated to the ADE 16. A terminal COM 1 of the PLC 20 is coupled to the ADE 16 to provide a common return line for the REJ signal, while a terminal COM 2 is coupled to the ADE 16 to provide a common return line for the ACC signal and for an ENTER signal, discussed below.

As previously noted, the relays CR0, CR1 and CR2 allow signals to be communicated between the PLC 20 and the ADS vision system 14 and the ADE 16 without direct electrical interconnection therebetween. This allows for communication between components which are incompatible because of different electrical signaling systems. In the present example, the PLC 20 uses 0 volt and 24 volt digital signaling, whereas the ADS vision system 14 uses TT, or transistor-to-transistor logic signaling based on 5 volt and 0 volt logic levels. The relays CR0 and CR1 are coupled by a common return line to the terminal 12 of the ADS vision system 14 at the +5 volt level.

When the relay contacts CR0 or CR1 are closed in response to accept or reject signal indications at the ADS vision system 14, the PLC 20 responds by communicating an ACC signal or an REJ signal from the terminals Y6 or Y2 thereof to the ADE 16 in the manner described above. Because the ADE 16 requires a separate ENTER signal following receipt of either an ACC signal or an REJ signal, the PLC 20 follows the generation of an ACC signal or an REJ signal with the generation of an ENTER signal, after an appropriate time delay which is determined by the PLC 20. Closure of a pair of contacts 36 in the PLC 20 provides the ENTER signal to the ADE 16 from terminal Y7 of the PLC 20, with the lead coupled to the terminal COM2 providing the return line therefor.

Figure 3:
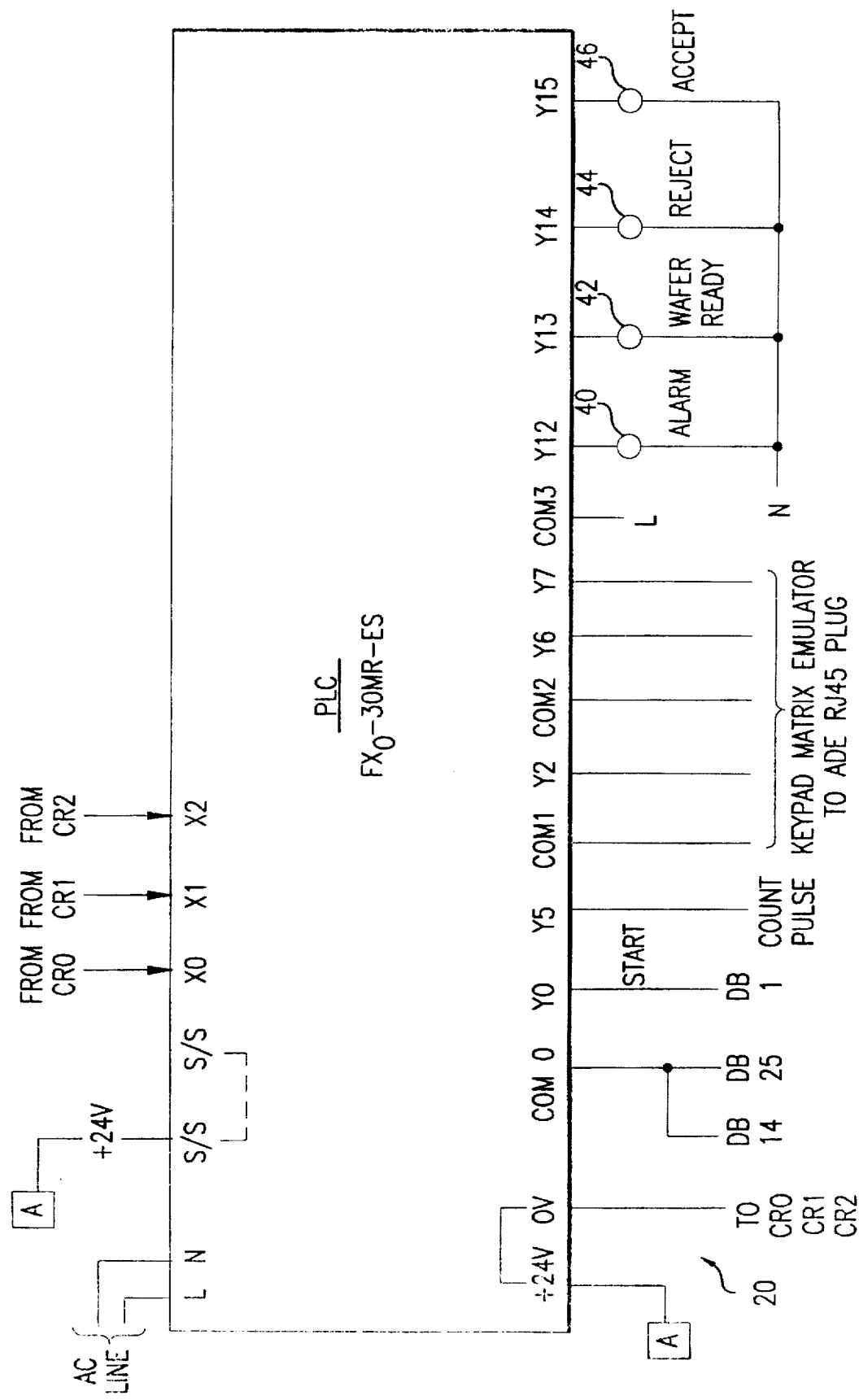
FIG. 3 is a schematic diagram showing the programmable logic controller of the interface system in greater detail.

The Mitsubishi $FX_0$-30MR-ES programmable logic circuit, which forms the major portion of the PLC 20, is shown in somewhat greater detail in FIG. 3, particularly with respect to the various terminals thereof. Only those terminals which are used are shown in FIG. 3, with the other terminals being omitted. As seen in the upper left of FIG. 3, the terminals L and N are coupled to an AC line. The common return terminals S/S are coupled to the relay board containing the relays CR0, CR1 and CR2, as is the +24 V terminal shown at the lower left of FIG. 3. The terminal 0V, shown at the lower left of FIG. 3, is coupled to the relay board. The terminal 0V is also coupled through the contacts of the relays CR0, CR1 and CR2 to the terminals X0, X1 and X2, respectively.

As shown in the lower portion of FIG. 3, the terminal Y0 provides the start signal to the terminal 1 of the ADS vision system 14. The terminal Y0 is also coupled to the terminal COM 0 through the contacts 30 within the PLC 20, as shown in FIG. 2. A terminal Y5 provides a count pulse. The terminals COM 1, Y2, COM 2, Y6 and Y7 are coupled to the keypad plug RJ45 of the ADE 16 as described in connection with FIG. 2, and as such provide a keypad matrix emulator to the ADE 16.

Not previously described in connection with FIG. 2 is the fact that several terminals of the PLC 20 are used to provide warning lights. As shown at the lower right of Fig. 3, the terminals Y12, Y13, Y14 and Y15 are coupled through lamps 40, 42, 44 and 46, respectively, to a terminal COM 3 which provides a common return. The lamp 40 is illuminated to provide an alarm whenever the ADS vision system 14 takes longer than 10 seconds to provide an ACC or REJ signal to the PLC 20, as described hereafter in connection with FIG. 4. The lamp 42 is illuminated when the ADE 16 determines that the wafer is ready for optical analysis by the ADS vision system 14. Lamps 44 and 46 respectively indicate when reject or accept signals are provided by the ADS vision system 14.

Figure 4:
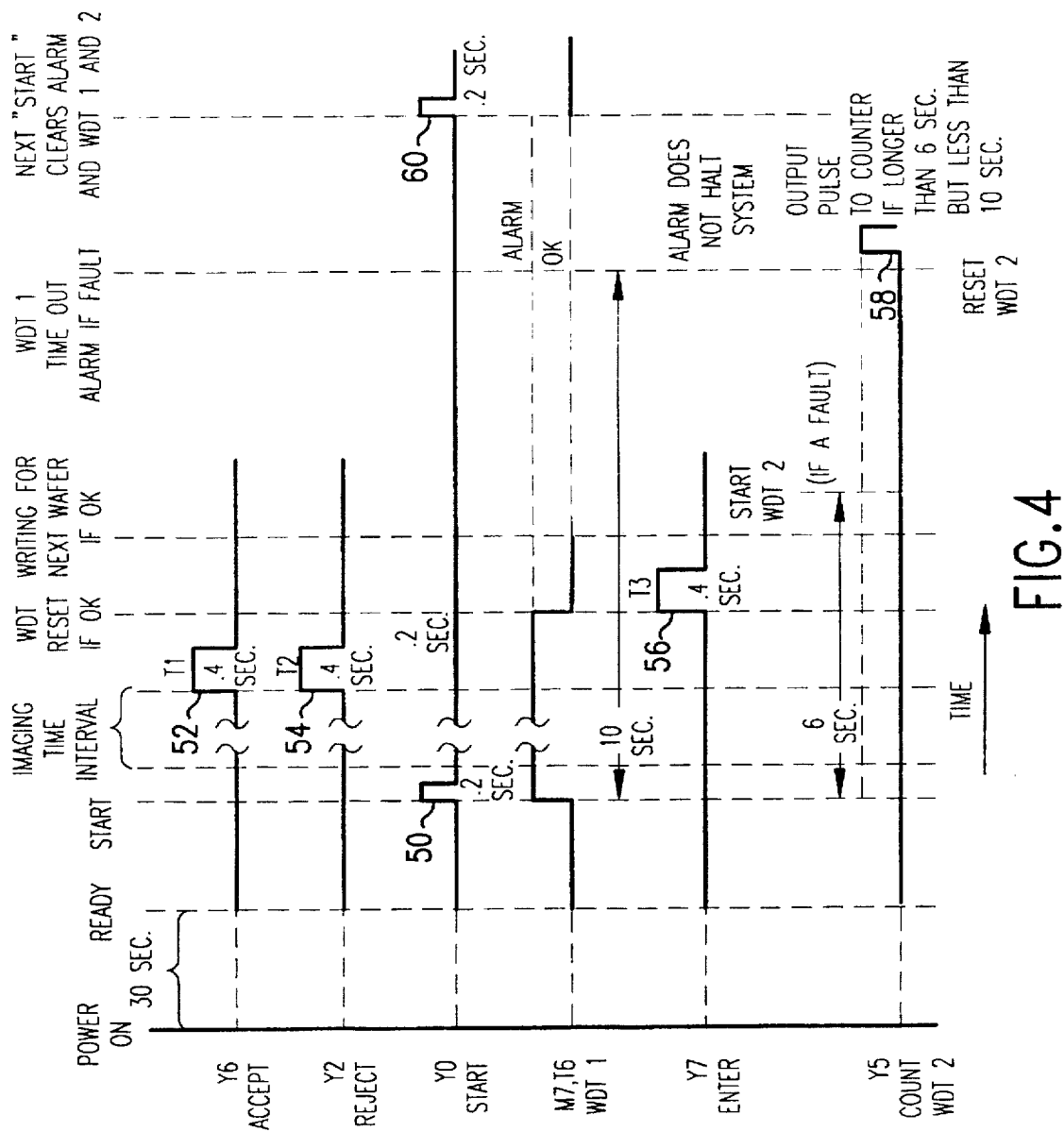
FIG. 4 is a timing diagram showing the manner in which various signals are communicated between the ADS vision system and the ADE by the interface system in conjunction with various time delay intervals.

The timing diagram of FIG. 4 helps to further explain the operation of the arrangement of FIG. 2. Following turn-on of the power to the system, a 30 second interval determined by a timer in the PLC 20 occurs to allow the system to warm up. During this 30 second power on interval, all inputs and outputs of the system are ignored. At the end of the 30 second interval, the system is ready for operation.

When the ADE 16 determines that the wafer is ready for optical analysis by the ADS vision system 14, the PLC 20 responds by providing the START signal to the ADS vision system 14 in the manner previously described. As shown in FIG. 4, the START signal consists of a pulse 50 of 0.2 seconds duration, as determined by a timer within the PLC 20. A start pulse of this configuration conforms to the time window of the ADE 16, and eliminates any noise which might otherwise be present. Coincident with the generation of the start pulse 50, a solid state switch M7 within the PLC 20 is activated to begin a 10.0 seconds timer T6, defining a first watchdog timer (WDT1). If it takes more than 10 seconds for the ADS vision system 14 to provide an ACC or REJ signal to the PLC 20, the lamp 40 shown in FIG. 3 is illuminated to indicate an alarm condition. A still further timer is initiated in coincidence with the occurrence of the start pulse 50. This is a 6.0 second time delay. If the ADS vision system 14 has not provided an ACC or REJ signal by the end of such delay, then a fault condition is determined and a second watchdog timer, WDT2, is started.

Following generation of the start pulse 50, an imaging time interval occurs during which the ADS vision system 14 optically analyzes the wafer and provides an ACC or REJ signal to the PLC 20. Typically, the imaging time interval is approximately 3–4 seconds in duration. If the imaging time interval results in a signal indication at the terminal 2 of the ADS vision system 14, then a timer Ti within the PLC 20 generates and provides to the ADE 16 an ACC signal in the form of a pulse 52 of 0.4 seconds duration. Conversely, if the ADS vision system 14 provides a signal indication at the terminal 3 thereof, a timer T2 within the PLC 20 provides to the ADL 16 an RFJ signal in the form of a pulse 54 of 0.4 seconds duration. After a 0.2 second delay from the end of the pulse 52 or the pulse 54, as determined by the PLC 20, a timer T3 within the PLC 20 generates an enter signal in the form of a pulse 56 of 0.4 seconds duration. The 0.2 second delay between termination of the pulse 52 or 54 and the occurrence of the enter pulse 56 is commensurate with the timing of the ADE 16 which requires receipt of the enter signal shortly after either the ACC signal or the REJ signal is received. If the enter pulse 56 is generated before the end of the 6.0 second interval, it is determined that the timing of the ADS vision system 14 is "OK" and both watchdog timers WDT1 and WDT2 are reset. After a short delay, the system is ready for the next wafer within the ADE 16 to be optically analyzed by the ADS vision system 14.

If the ADS vision system 14 takes longer than 6.0 seconds but less than 10.0 seconds to complete its optical analysis and provide either an ACC or an REJ signal indication, then a fault condition is determined. At the end of the 6.0 second interval the second watchdog timer WDT2 is started. A counter within the PLC 20, which keeps a record of the number of times the ADS vision system 14 takes longer than 6.0 seconds to complete its analysis, is incremented. This provides a continuously updated record of the tardiness of the ADS vision system 14. The pulse for incrementing the counter to indicate that the ADS vision system 14 took longer than 6.0 seconds but less than 10.0 seconds is not generated until shortly after the end of the 10.0 second interval. Such pulse 58 is shown in FIG. 4.

If it takes longer than the 10.0 second interval for the ADS vision system 14 to complete its analysis and provide an ACC or REJ signal indication, then an alarm condition is indicated by turning on the lamp 40 shown in FIG. 3. However, the alarm does not halt the system. Upon occurrence of the next START signal, as represented by a pulse 60 in Fig. 4, the alarm condition is cleared as are both watchdog timers WDT1 and 2.

While various forms and modifications have been suggested, it will be appreciated that the invention is not limited thereto but encompasses all expedients and variations falling within the scope of the appended claims.

What is claimed is:

1. An arrangement for analyzing semiconductor wafers, comprising the combination of:

automated dimensioning equipment for examining wafers for selected characteristics;

a wafer image vision system for providing optical analysis of wafers in the wafer analysis system, the wafer image vision system having electrical signal incompatibility with the automated dimensioning equipment; and a communication interface system coupled to the automated dimensioning equipment and to the wafer image vision system and providing an automated interface between the wafer image vision system and the automated dimensioning equipment, the interface system being responsive to signals in the automated dimensioning equipment to provide corresponding signals to the wafer image vision system that are compatible therewith and to signals in the wafer image vision system to provide corresponding signals to the automated dimensioning equipment that are compatible therewith.

2. An arrangement in accordance with claim 1, wherein the interface system includes relays for communicating signals between the interface system and the automated dimensioning equipment and the wafer image vision system, and timers for providing time intervals and time delays in processing the signals provided to the wafer image vision system and to the automated dimensioning equipment.

3. An arrangement in accordance with the claim 1, wherein the interface system includes a programmable logic controller having an operating program, and a plurality of solid state relays coupling the interface system to the automated dimensioning equipment and to the wafer image vision system.

4. An arrangement in accordance with claim 3, wherein the interface system includes a plurality of lamps coupled to the programmable logic controller to provide visual indications of various operating conditions within the interface system, the automated dimensioning equipment and the wafer image vision system.

5. An arrangement in accordance with claim 3, wherein the controller executes a plurality of different counts to provide signals and delays of selected duration.

6. An arrangement in accordance with claim 1, wherein the interface system provides a start signal to the wafer image vision system in response to a signal indication in the automated dimensioning equipment that a wafer is ready for optical analysis by the wafer image vision system, and an accept or reject signal to the automated dimensioning equipment in response to a signal indication in the wafer image vision system representing the result of optical analysis of the wafer.

7. An arrangement in accordance with claim 6, wherein the interface system provides an enter signal to the automated dimensioning equipment after a selected time delay following provision of an accept or reject signal to the automated dimensioning equipment.

8. An arrangement in accordance with claim 6, wherein the interface system includes means for keeping a record of delays greater than a predetermined time delay in the provision of an accept or reject signal following the provision of a start signal to the wafer image vision system.

9. An arrangement in accordance with claim 8, wherein the interface system includes means for providing an alarm in the event of a delay greater than a second predetermined time delay in the provision of an accept or reject signal following the provision of a start signal to the wafer image vision system.

10. A communication interface system for use with a wafer image vision system and automated dimensioning equipment, comprising the combination of:

means responsive to a condition in automated dimensioning equipment that a wafer is ready for optical analysis for generating a start signal compatible with a wafer image vision system;

means responsive to generation of the start signal for initiating a first predetermined time interval;

means responsive to generation of the start signal for initiating a second predetermined time interval longer than the first predetermined time interval;

means responsive to a condition in a wafer image vision system for generating an accept or reject signal compatible with automated dimensioning equipment;

means responsive to generation of an accept or reject signal for generating an enter signal compatible with automated dimensioning equipment after a third predetermined time interval;

counter means coupled to be incremented each time an accept or reject signal is generated after the first predetermined time interval has occurred but before the second predetermined time interval has occurred;

means for providing an alarm each time an accept or reject signal is generated after the second predetermined time interval has occurred.

11. A communication interface system in accordance with claim 10, wherein the start signal is of approximately 0.2 seconds duration, the accept or reject signal is of approximately 0.4 seconds duration, the enter signal is of approximately 0.4 seconds duration, the first predetermined time interval is of approximately 6.0 seconds duration and the second predetermined time interval is of approximately 10.0 seconds duration.

12. A communication interface system in accordance with claim 10, wherein the interface system is comprised of a programmable logic controller which provides timers determining the duration of the start signal, the first and second predetermined time intervals, the accept or reject signal, and the enter signal.

13. A communication interface system in accordance with claim 12, further including a plurality of solid state relays, each having a coil for coupling to either a wafer image vision system or automated dimensioning equipment and electronic switches coupled to the controller.

14. A method of interfacing a wafer image vision system with automated dimensioning equipment, comprising the steps of:

responding to a signal indication in the automated dimensioning equipment that a wafer is ready for optical analysis by the wafer image vision system by generating a start pulse of predetermined duration and applying the start pulse to the wafer image vision system;

simultaneously with the generation of a start pulse, initiating at least one count of predetermined duration;

responding to an accept or reject signal indication in the wafer image vision system by generating an accept or reject signal of predetermined duration and applying the accept or reject signal to the automated dimensioning equipment;

responding to the generation of an accept or reject signal by generating an enter pulse of predetermined duration after a predetermined delay following termination of an accept or reject signal and applying the enter pulse to the automated dimensioning equipment; and determining that a fault condition exists if an accept or reject signal is generated after the at least one count has ended.

15. A method in accordance with claim 14, including the further steps of simultaneously with the generation of a start pulse, initiating a second Count of predetermined duration greater than the at least one count of predetermined duration, and determining that an alarm condition exists if an accept or reject signal is generated after the second count has ended.

16. A method in accordance with claim 14, wherein the steps of generating start, accept or reject and enter pulses include performing predetermined counts to provide the pulses with predetermined durations.

* * * * *